United States Patent [19]

Modica et al.

[11] Patent Number: 5,447,054
[45] Date of Patent: Sep. 5, 1995

[54] GAS SENSORS FORMED OF THIN TIN OXIDE FILMS, FOR GASEOUS HYDRO-CARBON DETERMINATION

[75] Inventors: Luigi Modica; Lucio De Angelis, both of Rome, Italy

[73] Assignees: Eniricerche S.p.A.; SNAM S.p.A., both of Milan, Italy

[21] Appl. No.: 314,370

[22] Filed: Sep. 28, 1994

Related U.S. Application Data

[63] Continuation of Ser. No. 27,558, Mar. 8, 1993, abandoned, which is a continuation of Ser. No. 662,781, Mar. 1, 1991, abandoned.

[30] Foreign Application Priority Data

Mar. 2, 1990 [IT] Italy ..................... 19535/90

[51] Int. Cl.⁶ ............................................. G01N 31/00
[52] U.S. Cl. ................................................. 73/31.06
[58] Field of Search ............ 340/634; 73/23.01, 31.05, 73/31.06; 422/98; 338/35, 34

[56] References Cited

U.S. PATENT DOCUMENTS

| | | | |
|---|---|---|---|
| 4,169,369 | 10/1979 | Chang | 73/31.06 |
| 4,250,737 | 2/1981 | Biglin | 73/23.2 |
| 4,399,684 | 8/1983 | Advani | 73/23.2 |
| 4,457,161 | 7/1984 | Iwanaga et al. | 73/23.2 |
| 4,485,667 | 12/1984 | Laluze et al. | 73/31.06 |
| 4,490,715 | 12/1984 | Kusanagi et al. | 338/34 |
| 4,535,315 | 8/1985 | Sakai | 73/31.06 |
| 4,542,640 | 9/1985 | Clifford | 73/23 |
| 4,572,900 | 2/1986 | Wohltjen | 73/31.06 |
| 4,584,867 | 5/1986 | Forster | 73/31.05 |
| 4,654,624 | 3/1987 | Hagan et al. | 338/34 |
| 4,706,493 | 11/1987 | Chang et al. | 73/31.06 |
| 4,792,433 | 12/1988 | Katsura et al. | 73/31.06 |

FOREIGN PATENT DOCUMENTS

| | | |
|---|---|---|
| 0141089 | 5/1985 | European Pat. Off. |
| 60-117139 | 6/1985 | Japan . |
| 61-155848 | 7/1986 | Japan . |
| 2170913 | 8/1986 | United Kingdom . |

*Primary Examiner*—Sandra L. O'Shea
*Assistant Examiner*—Raymond Mah
*Attorney, Agent, or Firm*—Robert D. Schaffer; Rogers and Wells

[57] ABSTRACT

For sensing gaseous hydrocarbons in a gas mixture, a device consisting of two sensitive elements, one being a reference element, which are heated to different temperatures. The sensors, formed by subjecting films deposited by silk-screen processes to heat treatment at high temperature, are connected to an electronic evaluation circuit.

20 Claims, 5 Drawing Sheets

FIG. 2A
FIG. 2C
FIG. 2B
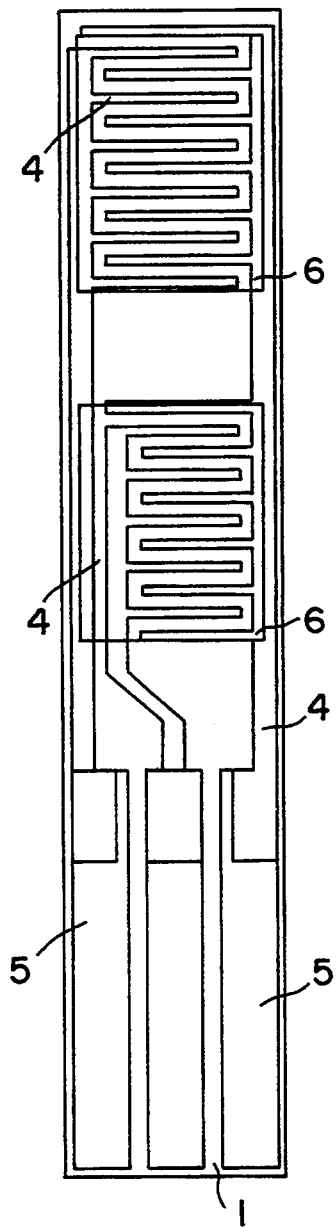
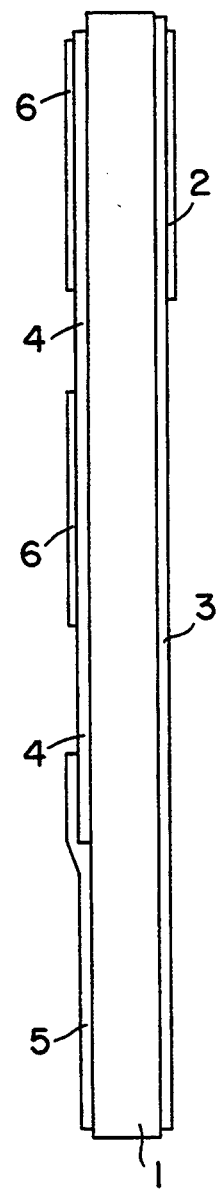
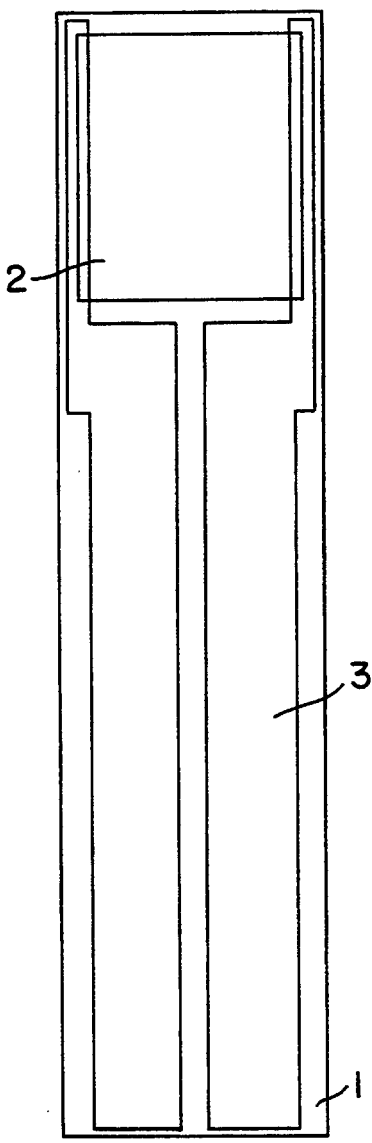

GAS SENSORS FORMED OF THIN TIN OXIDE FILMS, FOR GASEOUS HYDRO-CARBON DETERMINATION

This is a continuation of application Ser. No. 08/027,558, filed Mar. 8, 1993, (now abandoned) which is, in turn a continuation of Ser. No. 07/662,781, filed Mar. 1, 1991, now abandoned.

BACKGROUND OF THE INVENTION

1. Field of the Invention

This invention relates to a device comprising two sensitive elements, one of which is a reference element, for determining the presence of gaseous hydrocarbons in a gas mixture. The construction of easy to read portable instruments able to detect methane or other gaseous hydrocarbons requires the development of highly sensitive low-cost sensors.

2. Description of the Related Art

Since it was discovered, about 30 years ago, that the adsorption of a gas on the surface of a semiconductor produces a variation in the electrical resistance of the material and that this effect disappears as soon as the causes which generate it are eliminated, it has been sought to utilize these properties in the construction of simple low-cost gas sensors. Semiconductor sensors, generally of tin oxide, were developed initially to provide an alarm signal for natural gas, carbon monoxide, hydrogen and alcohol vapours. Sensors of this type are described in Chemical Sensor Technology ed. Tetsuro Seijama Elsevier 1988. Perfecting this type of sensor has been rather slow and difficult. The reason for this is that a semiconductor sensor is intrinsically unselective, in that it is sensitive not to a single species but to all species which have the same surface impact on it. Other problems are connected with stability and reproducibility.

A common drawback of this type of sensor is that before being put into operation it requires a long period of conditioning at the operating temperature.

Selectivity, stability and reproducibility are the main problems which have to be solved for the large-scale introduction of these low-cost devices.

Stability and reproducibility can be improved mainly by improving the method of construction of the sensitive element, whereas improving selectivity involves not only seeking new materials or catalysts sensitive to a particular type of gas, but also constructing arrays as described in U.S. Pat. Nos. 4,457,161 and 4,542,640. The array is an assembly of sensors each of which reacts differently on interaction with a gas mixture, to thus provide different responses. By processing these responses a given gaseous chemical species present in the environment in which the sensor is immersed can be distinguished. However this response analysis is made difficult by the low stability and poor reproducibility of each individual sensor.

It has now been found that these drawbacks can be overcome by a gas alarm sensor device consisting of two sensitive elements in the form of thin tin oxide films applied by a silk-screen process, one of which being a reference element, and which are heated to different temperatures.

SUMMARY OF THE INVENTION

In accordance therewith the present invention provides a sensor device for methane and other gaseous hydrocarbons such as propane and butane, comprising: two sensitive elements formed from a thin film based on tin oxide containing platinum; characterised in that:

one of the two sensitive elements is taken as the reference element, said two sensitive elements are heated to different temperatures, the sensitive elements being obtained by depositing on a support by a silk-screen process a metallorganic compound of tin containing platinum and subjecting it to heat treatment at high temperature;

said two sensitive elements being operationally connected to an electronic evaluation circuit able to:

measure the variations in the conductance of the two sensitive elements which arise by interaction with the gas, compare the signals emitted by the reference element and by the other element, and evaluate the gas presence and concentration on the basis of said signal comparison.

The films forming the sensitive part of the sensor elements, the resistors and the electronic contacts are deposited by a procedure comprising the following stages.

a) Silk-screen deposition. Film deposition by a silk-screen process using a commercial apparatus.

b) Levelling As the film silk-screen deposited in this manner has on its surface a line grid formed by the impression of the frame screen, this defect is eliminated by leaving the specimen for a few minutes in air at ambient temperature.

c) Drying. This is done in a commercial oven at a temperature of between 90° and 200° C. In this stage the more volatile substances of the silk-screen paste are removed with a weight loss of about 87%. The film acquires a certain consistency.

d) High-temperature curing. The curing of a silk-screen film is a rather complex process in which the organic solvents and binders are removed and the metal elements oxidized. Curing is carried out in a furnace at a temperature of between 400° and 1000° C. A typical device is formed in the following manner.

BRIEF DESCRIPTION OF THE DRAWINGS

FIG. 2A is a plan view illustrating the sensitive side of another embodiment of the present invention.

FIG. 2B is a rear view illustrating the opposite side of the embodiment shown in FIG. 2A.

FIG. 2C is a side view of the embodiment illustrated in FIGS. 2A and 2B.

DESCRIPTION OF THE PREFERRED EMBODIMENT

Sensitive Element

Figure 1A:
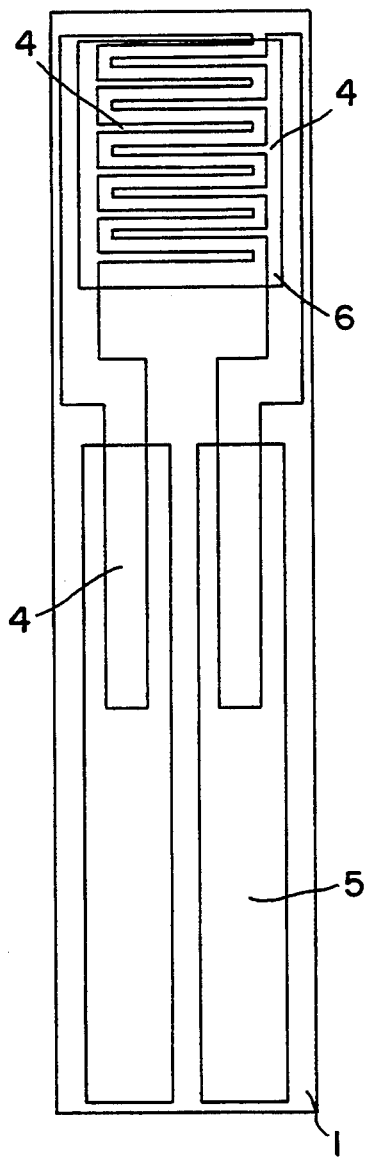
FIG. 1A is a plan view illustrating the sensitive side of one embodiment of the present invention.

FIG. 1 shows the sensitive side A, the opposite side B and a longitudinal section C of a sensor element. The heater is deposited by the method described in stages a) to d).

The heater 2, the purpose of which is to maintain the sensor at its optimum operating temperature, is deposited on an alumina plate 1 (6×25.4 mm) by a silk-screen process.

The commercial apparatus uses frames having a 325 mesh steel screen with its apertures positioned at 45°. The speed of the doctor blade is 0.3 sec for 60 mm and the thrust is 5.0 kg. The resistive paste is Du Pont HS 80 of 100 ohm/square.

After undergoing the levelling stage for 10 minutes the specimen is dried in an oven for 10 minutes at 125° C.

High temperature curing in effected in a belt furnace for 10 minutes at 850° C.

A heater is obtained measuring 5.6×5.8 mm with a resistance of about 100 ohms.

A conducting silk-screen paste based on platinum and gold is used to deposit the electrical contacts 3.

The conditions are as described for depositing the heater.

Contacts having a length of 24.4 mm and a width of 2.0 mm are obtained, superimposed on the heater for a length of 0.5 mm.

The electrical contacts 4 of the sensitive part are deposited on the opposite face to that on which the heater and its contacts are deposited.

The contacts 4, in the shape of a comb to obtain a low internal resistance of the sensitive element film, are formed in two parts by the process described for depositing the heater. For the comb-shaped part a gold-based metallorganic paste is used at a curing temperature of 820° C., enabling contacts of about 1 micron to be obtained (ESL cat. No. 8081). This small thickness, of the same order of magnitude as the sensitive part, facilitates uniform deposition of the sensitive part.

For the end part 5 of the contacts, the same paste as for the heater is used, to obtain a contact thickness of 7 microns.

The film forming the sensitive part 6 is now deposited using paste consisting of metallorganic tin with 10% of polypropylen glycol in terpineol and containing platinum metal in a quantity of less than 3% (preferably 1%) by weight on the tin oxide. The film can be deposited in a number of successive layers, by repeating the procedure used for the heater a number of times.

In a further embodiment of the sensor element, the films forming the sensitive part are deposited in accordance with stages a) to c) (silk-screen deposition, levelling and drying) repeated several times. The high-temperature roasting stage d) is then effected once only. The thickness of each of the films is about 0.2 microns.

The sensor element formed in this manner is then mounted on a connector.

Figure 1C:
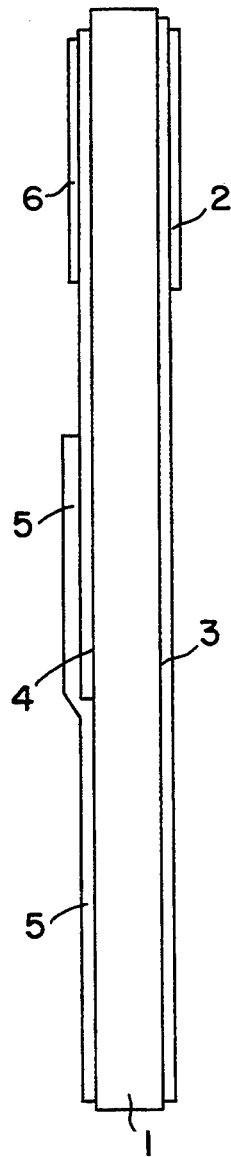
FIG. 1C is a side view of the embodiment illustrated in FIGS. 1A and 1B.
Figure 1B:
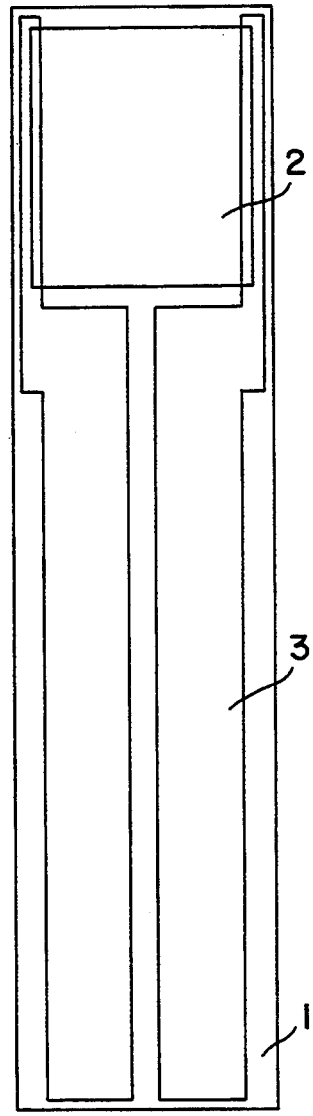
FIG. 1B is a rear view illustrating the opposite side of the embodiment shown in FIG. 1A.

In a further embodiment of the present invention the sensitive elements with their contacts are deposited on one side of a single alumina support, and a single heater with contacts is deposited at one end of the opposite face. FIG. 2 shows a sensor seen from the sensitive element side A, the heater side B and in longitudinal section C. The reference numerals have the same meaning as for FIG. 1. The resistor (heater) 2 is on an opposite face of the substrate as shown in FIGS. 1B and 1C. The resistor is for maintaining a temperature difference between the reference element and the measuring element of about 50°.

This geometry enables a temperature gradient to be obtained, so that the sensitive elements are at different temperatures although being on the same support.

In the different embodiments the thin film which forms the sensitive reference element can be deposited as a single silk-screen layer, while the film which forms the sensitive measuring element can be deposited as more silk-screen layers.

In each of its embodiments the constructed device has good stability and in particular needs a conditioning period of only about one hour at the operating temperature (200°–400° C. for the reference element and 400°–550° C. for the measuring element), whereas gas sensors normally require a conditioning period of some days in length.

Generally, the fact that in the embodiments of the present invention both the sensitive reference element and the sensitive measuring element are identical or indeed formed on the same support by a single process gives the device the advantage of high stability and measurement reproducibility.

The following examples further illustrate the invention but without limiting its scope.

EXAMPLE 1

Using the aforesaid procedures, a sensor device is constructed consisting of two sensitive elements connected to a single electronic control circuit by a standard connector. The sensitive elements are deposited by repeating steps a) to c) three times and applying step d) once only at the end. The chosen silk-screen paste contains 1% by weight of platinum metal (with respect to the dry tin oxide residue). The control unit enables the operating temperature of the two elements to be individually controlled continuously.

Figure 3:
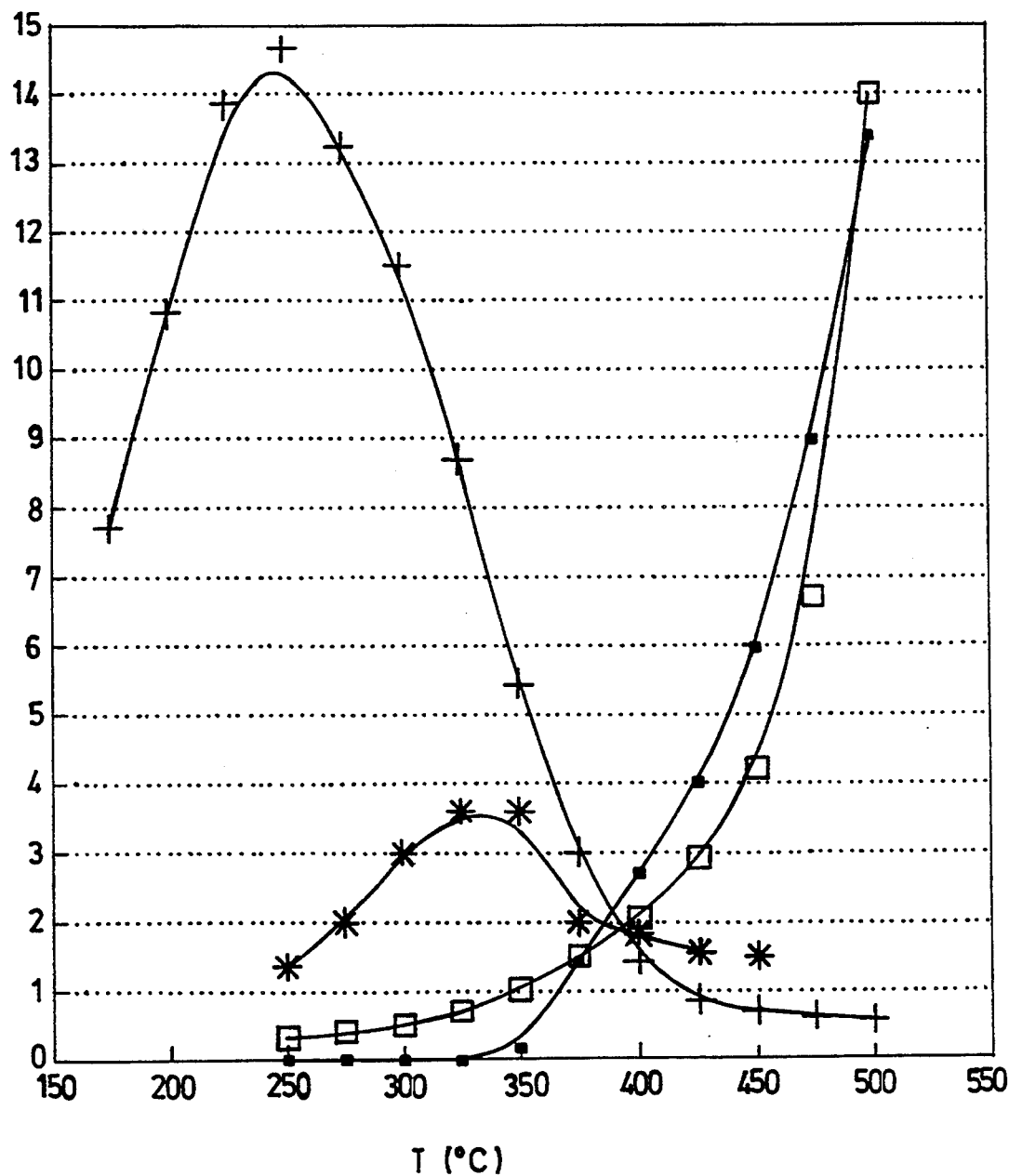
FIG. 3 is a graph representing the variation in conductance of the sensitive element for different types of gas or vapor.

In FIG. 3 the vertical axis represents variation in conductance of the sensitive element for certain types of gas or vapour, and the horizontal axis represents the sensor operating temperature. The curves relate to the following:

| | |
|---|---|
| ---□--□--- | 1% methane |
| --- --- --- | 1% butane |
| --■-■-- | 50 ppm carbon monoxide |
| ---+---+--- | 50 ppm ethanol. |

As can be seen, when at high temperature, in the 450°–500° C. range, the sensitive elements have high sensitivity for gases such as methane and butane. In contrast at low temperature, in the 250°–300° C. range, the sensitivity is high for the interfering gases such as ethanol and carbon monoxide.

As the control unit enables the temperature of the two sensitive element to be controlled individually, one of the elements, to be considered the reference element, can be operated within the low temperature range whereas the other can be operated within the high temperature range in which high sensitivity to hydrocarbon gases exists.

A device of this type can be used as an alarm sensor for hydrocarbons such as methane. In this case a suitable electronic circuit is able to evaluate the conductance variations of both the sensitive elements and to generate an alarm signal if it detects a higher conductance variation in the element maintained at higher temperature. If the higher conductance variation originates form the element maintained at lower temperature there would be no alarm, as an interfering gas is indicated as being present.

EXAMPLE 2

An alarm sensor device is constructed for gases such as methane or butane in the following manner.

Two sensitive elements formed of tin and platinum silk-screen film are deposited on the same side of an alumina plate. A heater is deposited on the opposite side, again by silk-screen deposition.

The geometry of the various sensor elements is such that on the face on which the sensitive elements are deposited there is a distribution of regions of substantially different temperatures.

In this manner one of the sensitive elements, taken as the reference element, can be operated at 300° C., i.e. in the range in which it is sensitive to interfering gases, and the other operated at 500° C.

The conditioning period at the predetermined operating temperatures is about one hour.

Having placed the device in the presence of a 1% methane-in-air mixture, a variation factor of 15 in the sensor conductance is measured for the range shown in FIG. 3, with relative emission of a visual or audible alarm. In this respect, it should be noted that the explosion threshold for methane is 4%.

EXAMPLE 3

An alarm sensor device is constructed for gases such as methane or butane, as described in the Example 2, the sensitive elements and the relative contact being deposited on the same side of a unique alumina plate and the unique heater and the relative contact being deposited at either end of the opposite side (see FIG. 2).

The difference, relative to the device described in the previous example, is that the film which forms the sensitive elements is deposited relative to the stages from a) to c) once only for the sensitive reference element and repeating the procedure thrice for the sensitive measuring element.

Eventually, the stage (d) of high temperature curing is carried out once for all, for all of the sensitive elements, both the reference elements and the measuring elements.

The conductance variations vs. the temperature of the sensitive measuring element of the so obtained device, are the same as those of the sensor device of Example 1, shown in FIG. 3.

Figure 4:
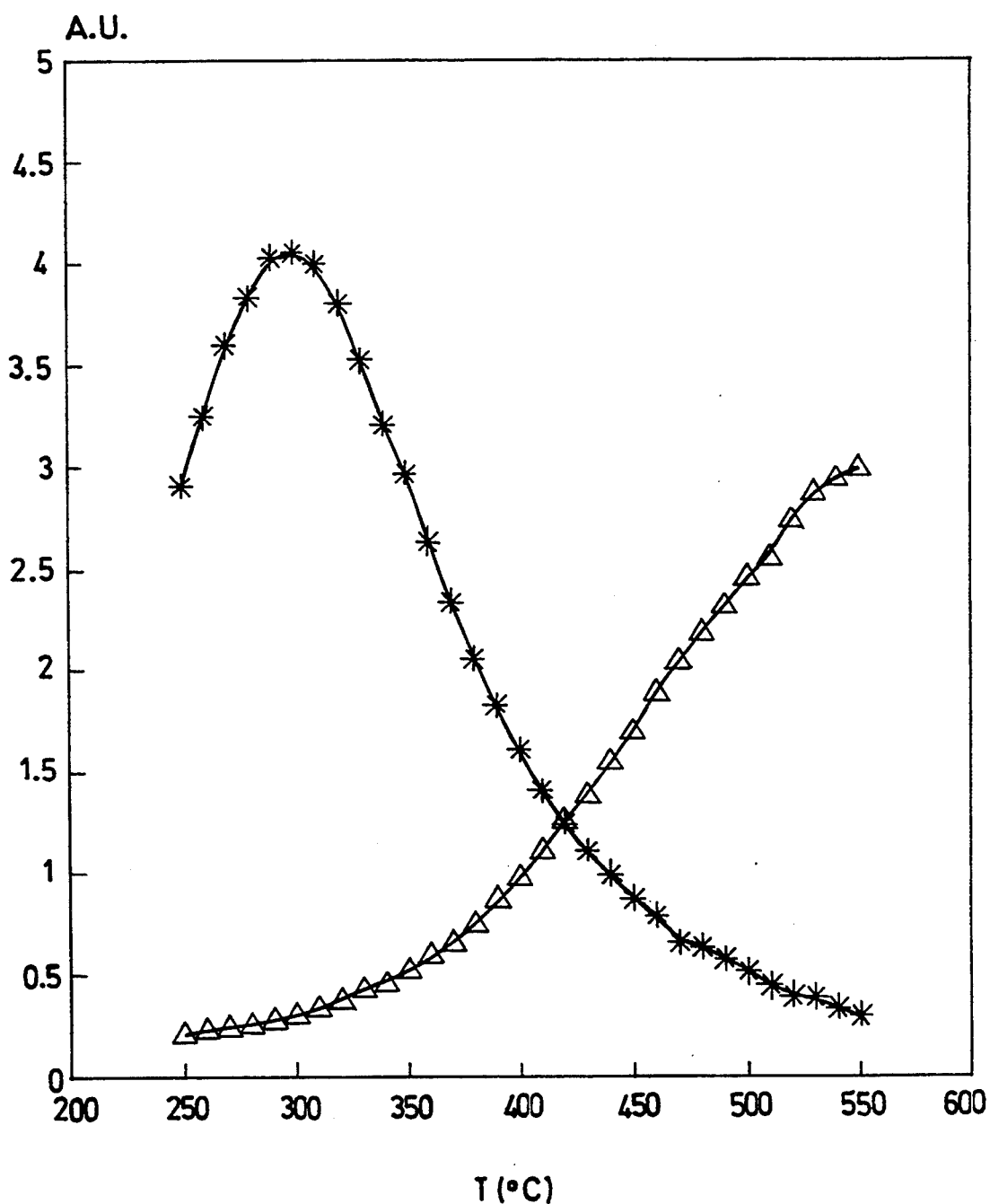
FIG. 4 is a graph representing the variation in sensitivity of the sensor as a function of the temperature of methane and ethanol.
Figure 5:
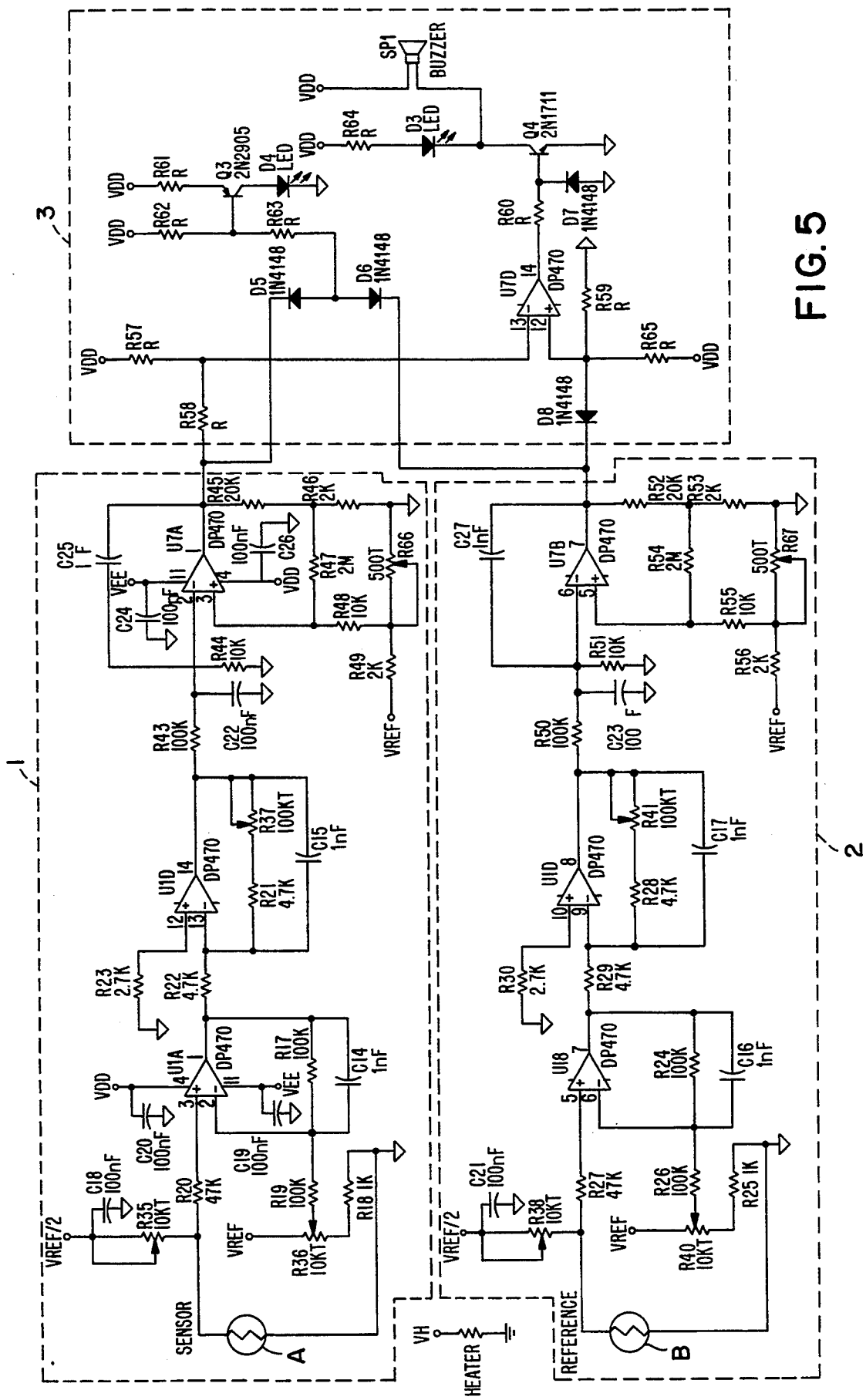
FIG. 5 is a circuitry layout diagram for the preferred embodiment of the present invention.

In connection with the reference sensitive element, which consist of a single layer of a semiconductor material, a sensitivity decrease is experienced for all the gases, by a factor of 4, said decrease being however associated to a considerable increase of the response speed. FIG. 4 shows the sensitivity variation as a function of the temperature of two gases, namely:

| | |
|---|---|
| --Δ--Δ-- | methane |
| --*--*-- | ethanol |

Such a behaviour may prove useful when using the subject device in environments in which high volumes of interfering gases might be present, so that a high response speed is imperative.

We claim:
1. A device having a substrate, wherein the device is for sensing hydrocarbons, comprising:
   a) a reference element positioned on the substrate for emitting a reference signal, wherein said reference element comprises a thin film of a metallorganic compound of tin oxide and platinum;
   b) a measuring element positioned on the substrate for sensing hydrocarbons and for emitting a measured signal representing said sensed hydrocarbons, wherein said measuring element comprises a thin film of a metallorganic compound of tin oxide and platinum;
   c) an electronic circuit connected to said reference element and said measuring element for comparing said reference signal with said measured signal and for emitting an evaluation signal representing said comparison; and
   d) an alarm connected to said evaluation signal, wherein said alarm is activated when said comparison reaches said reference signal; wherein each of said films comprise at least one layer and wherein each of said layers is about 0.2 microns thick.

2. The device of claim 1, wherein said films comprise three layers and wherein said layers are about 0.6 microns thick.

3. The device of claim 1, wherein said film of said reference element comprises a single layer and wherein said film of said measuring element comprises a plurality of layers.

4. The device of claim 3, wherein said film of said measuring element comprises three layers.

5. The device of claim 1, wherein said reference element and said measuring element are both positioned on the same face of the substrate.

6. The device of claim 5, further comprising a resistor positioned on a face opposite said same face of the substrate.

7. The device of claim 1, wherein said substrate comprises alumina.

8. The device of claim 1, further comprising a heater for maintaining the temperature of said reference element between about 200° C. and about 400° C. and for maintaining the temperature of said measuring element between about 400° C. and about 550° C.

9. The device of claim 1, further comprising a heater for maintaining about a 50° C. temperature difference between said reference element and said measuring element.

10. The device of claim 8, wherein said heater maintains the temperature of said reference element between about 250° C. and about 300° C. and maintains the temperature of said measuring element between about 450° C. and about 500° C.

11. The device of claim 1, wherein said alarm is activated when said measuring element senses butane.

12. The device of claim 1, wherein said alarm is activated when said measuring element senses propane.

13. A method for making a device for sensing hydrocarbons, comprising:
   a) selecting a substrate;
   b) depositing a first thin film of a metallorganic compound of tin oxide and platinum on said substrate for forming a reference element adapted for emitting a reference signal, wherein said first thin film is about 0.2 microns thick;

c) depositing a second thin film of a metallorganic compound of tin oxide and platinum on said substrate for forming a measuring element adapted for emitting a measured signal, wherein said second thin film is about 0.2 microns thick;

d) connecting an electronic circuit to said first and second films, wherein said circuit is adapted for comparing said reference signal with said measured signal and for emitting an evaluation signal representing said comparison; and e) connecting an alarm to said electronic circuit, wherein said alarm is activated when said comparison reaches said reference signal.

14. The method of claim 13, wherein said first film and said second film are silk screened deposited.

15. The method of claim 13, wherein said first film and said second film comprise at least one layer, wherein said layer is formed by depositing about 0.2 microns of said compound.

16. The method of claim 13, wherein said first film and said second film are formed by depositing three layers of said compound for forming a film of about 0.6 microns.

17. The method of claim 16, further comprising subjecting each of said layers to heat treatment after deposition of each layer.

18. The method of claim 16, further comprising subjecting said deposited layers to a single heat treatment after the last layer has been deposited.

19. The method of claim 13, further comprising subjecting said first film and said second film to a temperature between about 400° C. and about 1000° C.

20. A device having a substrate for sensing hydrocarbons, comprising:

a) a reference element positioned on the substrate for emitting a reference signal, wherein said reference element comprises three layers of a thin film of a metallorganic compound of tin oxide and platinum;

b) a measuring element positioned on the substrate for sensing hydrocarbons and for emitting a measured signal representing said sensed hydrocarbons, wherein said measuring element comprises three layers of a thin film of a metallorganic compound of tin oxide and platinum and wherein said thin film of said reference element and said thin film of said measuring element have a total thickness of about 0.6 microns and are subjected to a single high temperature treatment; and c) an electronic circuit connected to said reference element and said measuring element for comparing said reference signal with said measured signal and for emitting an evaluation signal representing said comparison.

* * * * *